United States Patent [19]    [11]  4,257,962
Szabo et al.    [45]  Mar. 24, 1981

[54] DERIVATIVES OF BICYCLIC LACTOLS

[75] Inventors: Tibor Szabó; Laszlo Institoris; Gábor Kovács; Gyula Dalmadi; Béla Kószegi; Istvan Stadlér, all of Budapest, Hungary

[73] Assignee: Chinoin Gyogyszer es Vegyeszeti Termekek Gyara Rt., Budapest, Hungary

[21] Appl. No.: 942,819

[22] Filed: Sep. 15, 1978

[30] Foreign Application Priority Data

Sep. 26, 1977 [HU] Hungary .................. CI 1771

[51] Int. Cl.³ .................................. C07D 307/935
[52] U.S. Cl. .................. 260/346.22; 260/346.73; 424/285
[58] Field of Search ............ 536/4, 115; 260/346.22, 260/346.73

[56] References Cited

U.S. PATENT DOCUMENTS

| | | | |
|---|---|---|---|
| 3,023,183 | 2/1962 | Nelson | 536/118 |
| 3,657,328 | 4/1972 | Finch | 536/18 |
| 3,914,258 | 10/1975 | Woodward | 260/346.22 |
| 3,975,406 | 8/1976 | Mayer et al. | 260/346.22 |
| 3,987,085 | 10/1976 | Yankee | 260/346.22 |
| 4,036,871 | 7/1977 | Holland et al. | 260/346.22 |
| 4,041,064 | 8/1977 | Gandolfi et al. | 260/346.22 |
| 4,064,351 | 12/1977 | Sakai et al. | 260/346.22 |
| 4,094,886 | 6/1978 | Kondo et al. | 260/346.22 |

OTHER PUBLICATIONS

Brewster et al., J. Chem. Society Perkin I (1973) pp. 2796–2804.
Chemical Abstracts, 9th Collective Index, p. 12874cs.

Primary Examiner—Henry R. Jiles
Assistant Examiner—Bernard Dentz
Attorney, Agent, or Firm—Karl F. Ross

[57] ABSTRACT

Racemic or optically active compounds with antitumor activity of the formula:

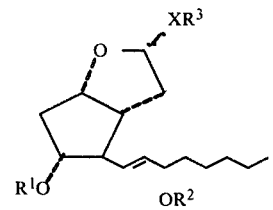

wherein
X is oxygen or sulfur;
$R^1$ is hydrogen, $C_1$ to $C_4$ alkanoyl, benzoyl or phenyl-substituted benzoyl;
$R^2$ is hydrogen or $C_1$ to $C_4$ alkanoyl;
$R^3$ is $C_2$ to $C_{40}$ straight or branched chain alkyl substituted by hydroxy, epoxy, amino, $C_1$ to $C_6$ alkylamino, $C_1$ to $C_6$ dialkylamino, $C_1$ to $C_6$ alkanoyloxy or, $C_1$ to $C_4$ alkoxycarbonyl; cyclohexyl, phenyl unsubstituted or substituted by halogen, amino, $C_1$ to $C_4$ alkyl-substituted amino, $C_1$ to $C_4$ alkoxy, nitro, or hydroxy; $C_1$ to $C_6$ alkanoyl; allyl or phenyl-$C_1$ to $C_4$ alkyl unsubstituted or substituted by a $C_2$ to $C_6$ alkene group; or where X is sulfur $R^3$ is as defined above or is $C_1$ to $C_{40}$ straight or branched chain alkyl; and
~ represents the exo- or endo-steric position in the ring and indicates an α- or β-steric position in the side chain are disclosed.

4 Claims, No Drawings

DERIVATIVES OF BICYCLIC LACTOLS

The present invention relates to new racemic and optically active semi-prostanoid compounds, a process for the preparation of the same and pharmaceutical compositions containing as active ingredient the above compounds. The new compounds have a structure of the formula I

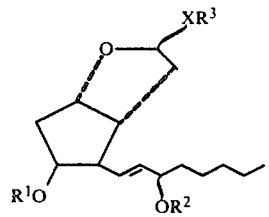

wherein
$R^1$ and $R^2$ are the same or different and stand for hydrogen, $C_{1-6}$ straight or branched alkanoyl or optionally substituted aroyl or aralkanoyl,
X is oxygen or sulphur,
$R^3$ is $C_{2-40}$ straight or branched alkyl, alkenyl, alkynyl or cycloalkyl optionally substituted by one or several hydroxy, carboxy, carbalkoxy, acyloxy, substituted or unsubstituted carboxamido, amino, oxo, cyano, nitro or epoxy groups and/or halogen atoms in any position and/or interrupted by one or several heteroatoms or optionally substituted aryl, aralkyl, or heteroaryl,
~ represents exo- or endo-steric position in the ring and indicates α or β (S or R) steric position in the side chain and
$R^3$ stands for hydrogen or methyl if X is sulphur.

Alkyl in the groups alkanoyl, aralkanoyl and alkyl in the definitions of $R^1$, $R^2$ and $R^3$ may consist of any branched or straight chain, which may optionally be interrupted by one or several heteroatoms, such as oxygen or sulphur and/or may be substituted. In the definitions of $R^1$, $R^2$ and $R^3$ the aromatic part of aryl and aralkyl groups may consist of one or several benzene rings formed by condensation of the rings or by connection with chemical bonds and may optionally be substituted or unsubstituted. Heteroaryl groups may include one or several heteroatoms, such as nitrogen, sulphur and/or oxygen, may be formed by one or several identical or different hetero or homocycles like the aromatic rings and may substituted or unsubstituted.

The substituents may be selected from lower alkyl, alkoxy, and alkylthio, halogen, trifluoromethyl, nitro, substituted and unsubstituted amino and carboxamido, hydroxy and carboxy and esterified derivatives thereof.

Particularly those compounds of the general formula I are preferred in which X and ~ are as defined above and
$R^1$ is hydrogen, $C_{1-4}$ alkanoyl, or optionally phenyl-substituted benzoyl,
$R^2$ stands for $C_{1-4}$ alkanoyl, hydrogen,
$R^3$ is $C_{2-20}$ straight or branched chained alkyl, optionally substituted with one or several hydroxy, epoxy, amino, $C_{1-6}$ alkylamino, $C_{1-6}$ dialkylamino, $C_{1-6}$ alkanoyloxy, $C_{1-4}$ alkoxycarbonyl and/or halogen; phenyl, optionally substituted with one or several halogen, amino, $C_{1-4}$ alkyl-substituted amino, $C_{1-4}$ alkoxy, nitro, hydroxy, groups; $C_{1-6}$ alkanoyl, phenyl-$C_{1-4}$ alkyl, wherein phenyl may optionally be substituted or a $C_{2-6}$ alkene group
$R^3$ may stand for hydrogen or methyl if X is sulphur.

According to the invention compounds of the formula I

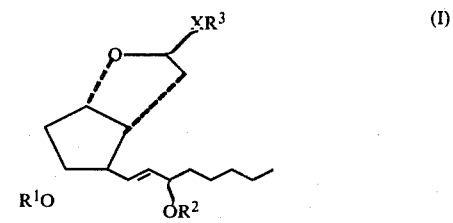

may be prepared by
(a) reacting compounds of the formula II

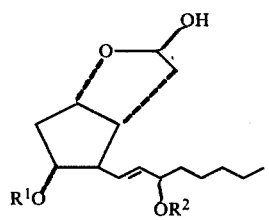

wherein $R^1$, $R^2$ and ~ are as defined above—with compounds of the formula III $$R^3-XH \qquad (III)$$

wherein X and $R^3$ are as defined above—in the presence of an acid catalyst or
(b) reacting compounds of the formula II—wherein $R^1$, $R^2$ and ~ are as defined above—with compounds of the formula IV $$R-CO-Y \qquad (IV)$$

wherein R is alkyl, preferably $C_{1-4}$ alkyl or aryl and Y stands for halogen or a group of the formula R—CO—O— wherein R is as defined above, optionally in the presence of an acid binding agent and reacting the obtained compounds of the formula V

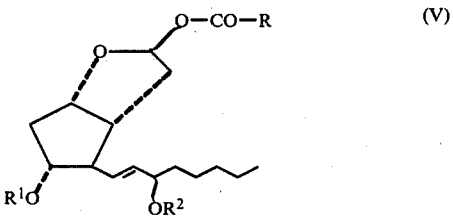

wherein $R^1$, $R^2$ and R are as defined above—with compounds of the formula III in the presence of an acid catalyst and introducing to the obtained compounds of the formula I, if desired, new substituents and/or converting the substituents in order to get new compounds of the formula I.

These additional conversions include replacing a group $R^3$ with another $R^3$, or optionally converting $R^3$ e.g. by acylation or by forming an epoxy group, or replacing $R^1$ and optionally $R^2$ different from hydrogen by hydrogen (desacylation) or acylating a compound of the formula I containing hydrogen in the place of $R^2$ and optionally of $R^1$. These additional conversions may be carried out at once or in several steps.

Compounds of the formula I may be formulated to pharmaceutical compositions of thrombocyte aggregation inhibiting, smooth muscle contracting and antitumor activity, e.g. in the form of tablets, dragées, injections, sub-lingual tablets in association with the generally used diluents and/or filling agents and/or formulation excipients.

Some representatives used as starting materials in the process of the invention of the formula II are known from prostaglandine synthesis according to Corey, and some other representatives may be prepared according to an analogous method to the process described in Hungarian patent application No. CI-1654, by reducing the appropriate oxo derivatives. According to the preferred process compounds of the formula II may be prepared in the form of stereochemically homogeneous, pure epimers or in the form of a mixture of racemic epimers containing substituents of $\alpha$ and $\beta$ steric positions in the positions 2- and/or 15.

According to the invention compounds of the formula II and V are reacted with compounds of the formula III in the presence of an acid catalyst. As acid catalysts inorganic acids or organic acids such as Lewis acids may be used. As such acids hydrochloric acid, p-toluene sulfonic acid and borotrifluoride etherate may be mentioned. The amount of the acid catalyst may be varied within a wide range. The reaction may be accelerated by increasing the amount of the acid, but a too high acid concentration may start detrimental decomposition processes or may induce side reactions.

0.1 mole acid is preferably used related to the lactol derivative of the formula II and related to the lactol derivative of the formula V. The reaction rate may be considerably increased by using a high excess of the compound of the formula III.

The reaction may preferably be carried out in the presence of an organic solvent. Dipolar, aprotic solvents, such as dimethylformamide and dimethylsulfoxide which have an outstanding solubility are particularly suitable. The reaction may also be performed in ether type solvents, chlorinated hydrocarbons, or in other solvents used in organic chemistry as well. If the compounds of the formula III are liquid under the circumstances of the reaction the compound of the formula III may simultaneously serve as a solvent if used in an excess.

The reaction temperature may be varied in a wide range. One may proceed at a lower or higher temperature than room temperature but room temperature is most preferred to carry out acetal formation.

The reaction may be well monitored by thin layer chromatography. The reaction mixture is either directly dropped on the layer or an aliquot part of the reaction mixture is first mixed with a 10% aqueous sodium-hydrogen carbonate solution, whereafter the mixture is extracted with ether or ether acetate and this organic extract is chromatographed.

When the reaction is completed the pH of the reaction mixture is adjusted to 7-8 by adding 10% aqueous sodium hydrogen carbonate solution whereafter the excess of the compound of the formula III is removed and the crude product is purified preferably by column chromatography. The compound of the formula III may be removed depending on its physical properties for example by distillation, extraction, or chromatography.

It is obvious, that if the used starting materials are epimeric mixtures, the compounds of the formula I are also obtained in the form of epimeric mixtures.

The epimeric mixtures may generally be separated by column chromatography. It is particularly favorable when separating epimers, if compounds of the formula II containing p-phenylbenzoyl as $R^1$ are used as starting materials. If $R^3$ in the end product contains free hydroxy this method cannot be employed. In this latter case exo and endo-isomers generally do not separate in the course of chromatography. If, however, the free hydroxy groups are protected with a known protective group, the separation may be carried out by chromatography.

If $R^7$ in the compounds of the formulae II or V stands for a group other than hydrogen, then the reaction with the compounds of the formula III gives acetal ester derivatives of the formula I. As the acetal structure is not sensible to bases, these compounds may be desacylated in a basic medium. The basic desacylation may preferably be carried out in methanolic medium with solid potassium carbonate. Compounds containing hydrogen in the place of $R^1$ and $R^2$ are obtained.

It has been found, that the exo epimers of the compounds of the formula I are crystalline substances and may be recovered from the epimeric mixture by fractionated crystallization.

As compounds of the formula III both alcohols of the formula $R^3$—OH and mercaptanes of the formula $R^3$-SH may be used and the reaction takes place substantially in the same way. As mercaptanes preferably n-butyl mercaptane and thiophenol may be employed.

As the reaction according to process variant (a) in an acid medium is an equilibrium reaction, the formation of the compounds of the formula I is promoted by using an excess of the compounds of the formula III, thus, it is possible if desired, to replace —$XR^3$ in the compounds of the formula I with another group of the formula $R^{3'}$—$X'$ by reacting the compound of the formula I in an acid medium with a compound of the formula $R^{3'}$—$X'$—H, wherein $R^{3'}$ and $X'$ are the same as $R^3$ and X as defined above, but at least one of them is different from —$XR^3$ of the compound of the formula I to be converted.

Thus for example if a compound of the formula I containing p-phenyl-benzoyl as $R^1$, hydrogen as $R^2$ and —S—$C_4H_9$ as —$XR^3$ is reacted with an excess of n-butanol in the presence of borotrifluoride-etherate a compound of the formula I is obtained, wherein—$XR^3$ is —O—$C_4H_9$— wherein $R^1$ and $R^2$ are the same as in the starting material. The conversion may be naturally carried out inversely by using butyl mercaptane.

Compounds of the formula I exhibit a valuable pharmacological activity. The compounds inhibit thrombocyte aggregation, act on the smooth muscles like prostaglandins, contracting thus the uterus strip, the stomach fundus and colonic longitudinal strip of rats. Some of the compounds show a prostaglandin antagonist activity reducing thus the spontaneous contraction of the uterus of rats and also the effects induced by $PGF_{2\alpha}$ on the same organ. The compounds also influence the cell metabolism and inhibit the DNS, RNS and protein synthesis in the tumor cells (measured by incorporation of $^3H$-thymidine). The tumor inhibiting activity may be shown in vivo too. The compounds inhibit the prostaglandin-dehydrogenase enzyme as well.

The compounds of the formula I exhibit these activities in a very low concentration and their toxicity is also very low ($LD_{50}$ in mice of a compound of the formula I wherein $-XR^3$ is exo-amyloxy, $R^1$ stands for hydrogen and $-OR^2$ is R-hydroxy- is 700 mg/kg bodyweight). Anticoagulant activity may be observed already at a concentration of 10 gamma/ml.

The further details of the invention are illustrated by the following Examples without limiting the scope of the invention to the Examples.

EXAMPLE 1

(−)-2,3,3aβ,6aβ-Tetrahydro-2-butyloxy-5α-(p-phenylbenzoyloxy)-4β-(3β-hydroxy-oct-1-trans-enyl)-cyclopentano[b]furan To a 50 ml. flask equipped withh a stirrer 4.505 g. (10 mmoles) of (−)-2,3,3aβ,6aβ-tetrahydro-2-hydroxy-5α-(p-phenylbenzoyloxy)-4β-(3β-hydroxy-oct-1-trans-enyl)-cyclopentano[b]furan are added. 18.2 ml. (200 mmoles) of n-butylalcohol, 0.05 ml. (0.5 mmole) of conc. sulphuric acid are then added. The reaction mixture is then stirred at room temperature and the reaction is followed by thin layer chromatography. The starting material is completely reacted within 10–15 minutes and two product spots appear, i.e. the spots of the exo-endo isomers. After the reaction is completed, the reaction mixture is neutralized with 0.42 g. (5 mmoles) of sodium hydrogen carbonate and a few drops of water, whereafter the excess of the alcohol is evaporated in vacuo.

The residue is subjected to chromatography on a column prepared of 225 g. silicagel, using a 6:1 mixture of benzene and ethyl acetate as eluting mixture. The fractions containing exo and endo epimers are evaporated separately. 2.94 g. (58%) of exo-epimer are obtained. The product crystallizes while removing the solvent. White prismatic crystals may be obtained by recrystallization from isopropylether-petrolether. Melting point: 48°–49° C. $R_f=0.52$, developed on 10 cm. high DC-Fertigplatten KIESELGEL thin layer in a saturated bath, in a 2:1 mixture of benzene and ethyl acetate. The front velocity of the solvent: 0.7 cm./min. Developer: phosphoro molybdenic acid.

IR peaks: 3490, 2970, 2930, 2880, 1720, 1610, 1460, 1410, 1275, 1180, 1120, 1100, 1045, 1000, 855, 780, 750, 700, $cm^{-1}$.

$C^{13}$ NMR chemical shifts (ppm): 45.66; 80.49; 38.79; 79.99; 53.95; 129.98; 136.62; 72.49; 37.22; 24.99; 31.77; 22.50; 13.96; 37.34; 105.38; 165.94; 127.00; 127.23; 128.13; 128.90; 130.11; 140.01; 145.72; 129.02; 13.86; 19.38; 31.77; 76.02.

Yield of endo epimer: 1.82 g. (36%). The product is a ororless thick oil, it does not crystallize.

$R_f$ value: 0.36. (Measured in a system described at the exo epimer).

IR peaks are the same as obtained for the exo epimer.

EXAMPLE 2

(−)-2,3,3aβ,6aβ-Tetrahydro-2-hexadecyloxy-5α-(p-phenylbenzoyloxy)-4β-(3α-hydroxy-oct-1-trans-enyl)-cyclopentano[b]furan To a 100 ml. flask equipped with a stirrer 4.505 g. (10 mmoles) of (−)-2,3,3aβ,6aβ-tetrahydro-2-hydroxy-5α-(p-phenylbenzoyloxy)-4β-(3α-hydroxy-oct-1-trans-enyl)-cyclopentano[b]furan are added, and 12.1 g. (50 mmoles) of cetyl alcohol and 48 ml. of anhydrous benzene are further added. When the substances are completely dissolved the reaction is initiated by adding 0.05 ml. (0.5 mmole) of concentrated hydrochloric acid. The reaction is completed within 10–15 minutes at room temperature. The exo and endo epimers of the product appear separately on the thin layer chromatogram. The reaction mixture is neutralized with 0.42 g. of sodium hydrogen carbonate and a few drops of water, the reaction mixture is filled to a column of 113 g. of silicagel and the product is eluted with a 6:1 mixture of benzene and ethyl acetate.

The solvent is removed from the fractions containing exo and endo epimers separately.

Yield of the exo epimer: 3.8 g. (58%).

$R_f$ (in the system described in Example 1): 0.67.

Yield of the endo epimer: 2.6 g. (36%);

$R_f$ (in the system described in Example 1): 0.51.

EXAMPLE 3

(−)-2,3,3aβ,6aβ-Tetrahydro-2-butyloxy-5α-(p-phenylbenzoyloxy)-4β-(3β-hydroxy-oct-1-trans-enyl)-cyclopentano[b]furan The process is carried out according to Example 1 but as starting material 5.20 g. (10 mmoles) of (−)-2,3,3aβ,6aβ-tetrahydro-2-endo-amyloxy-5α-(p-phenylbenzoyloxy)-4β-(3β-hydroxy-oct-1-trans-enyl)-cyclopentano[b]furan are used.

The reaction is followed by thin layer chromatography.

The preacetalyzation is completed within 10–15 minutes, but 1–5% of the starting material is remaining in the system. The reaction is accompanied by racemization. As a product an epimer-mixture is obtained. The mixture is further worked up and subjected to chromatography according to Example 1.

Yield of the obtained exo epimer: 2.8 g. (55%).

Yield of the obtained endo epimer: 1.65 g. (32.5%). The physical constants of the product are identical with the data described in Example 1.

EXAMPLE 4

1 mmole of the corresponding starting materials are reacted with the corresponding alcohols under the circumstances described above according to Examples 1, 2 and 3 and the following compounds are obtained:

(a) (−)-2,3,3aβ,6aβ-Tetrahydro-2-exo- and -endo-ethoxy-5α-(p-phenylbenzoyloxy)-4β-(3α- and 3β-hydroxy-oct-1-trans-enyl)-cyclopentano[b]furan, (b) (−)-2,3,3aβ,6aβ-Tetrahydro-2-exo- and -endo-isopropyloxy-5α-(p-phenylbenzoyloxy)-4β-(3α- and 3β-hydroxyoct-1-trans-enyl)-cyclopentano[b]furan, (c) (−)-2,3,3aβ,6aβ-Tetrahydro-2-exo- and endo-butoxy-5α-(p-phenylbenzoyloxy)-4β-(3α-hydroxy-oct-1-transenyl)-cyclopentano[b]furan, (d) (−)-2,3,3aβ,6aβ-Tetrahydro-2-exo- and -endo-isobutoxy-5α-(p-phenylbenzoyloxy)-4β-(3α- and 3β-hydroxy oct-1-trans-enyl)-cyclopentano[b]furan, (e) (−)-2,3,3aβ,6aβ-Tetrahydro-2-exo- and -endo-tert-butoxy-5α-(p-phenylbenzoyloxy)-4β-(3α- and 3β-hydroxy-oct-1-trans-enyl)-cyclopentano[b]furan, (f) (−)-2,3,3aβ,6aβ-Tetrahydro-2-exo- and -endo-amyloxy-5α-(p-phenylbenzoyloxy)-4β-(3α- and 3β-hydroxy-oct-1-trans-enyl)-cyclopentano[b]furan, (g) (−)-2,3,3aβ,6aβ-Tetrahydro-2-exo- and endo-hexadecyloxy-5α-(p-phenylbenzoyloxy)-4β-(3β-hydroxy-oct-1-trans-enyl)-cyclopentano[b]furan, (h) (−)-2,3,3aβ,6aβ-Tetrahydro-2-exo- and -endo-cyclohexyloxy-5α-(p-phenylbenzoyloxy)-4β-(3β-hydroxy-oct-1-transenyl)-cyclopentano[b]furan.

The $R_f$ values of the prepared compounds are summarized in the table below:

| Compound | $R_1$ values | | | |
| | α allyl-hydroxy | | β-allyl-hydroxy | |
| | exo epimer | endo epimer | exo epimer | endo epimer |
| --- | --- | --- | --- | --- |
| a. | 0.45 | 0.375 | 0.38 | 0.275 |
| b. | 0.50 | 0.41 | 0.43 | 0.32 |
| c. | 0.57 | 0.43 | — | — |
| d. | 0.59 | 0.45 | 0.55 | 0.37 |
| e. | 0.53 | 0.45 | 0.48 | 0.38 |
| f. | 0.60 | 0.46 | 0.56 | 0.40 |
| g. | — | — | 0.64 | 0.42 |
| h. | — | — | 0.60 | 0.47 |

EXAMPLE 5

(−)-2,3,3aβ,6aβ-Tetrahydro-2-pentyloxy-5α-hydroxy-4β-(3β-hydroxy-oct-1-trans-enyl)-cyclopentano[b]furan To a 50 ml. flask equipped with a stirrer 2.7 g. (10 mmoles) of (−)-2,3,3aβ,6aβ-tetrahydro-2,5α-dihydroxy-4β-(3β-hydroxy-oct-1-trans-enyl)-cyclopentano[b]furan are added. 14.7 ml. (150 mmoles) of n-amyl alcohol and 0.05 ml. (0.5 moles) of concentrated hydrochloric acid are further added, the later to initiate the reaction. The reaction is followed by thin layer chromatography, with ethyl acetate as a developing agent. The exo and endo epimers do not separate. The conversion is completed within ten minutes. No side product is formed. The reaction is stopped with 0.42 g. (5 mmoles) of sodium hydrogen carbonate in the presence of a few drops of water.

The alcohol excess is evaporated in vacuo and the residual oil is chromatographed on a column of 135 g. silicagel with a 1:1 mixture of benzene and ethyl acetate.

The solvent is removed and the obtained thick oil is allowed to stand for one day in a refrigerator, until it becomes solid. 3.1 g. of crude product are obtained (91%).

3.1 g. of the crystalline product are dissolved in 15 ml. of hot petrolether whereafter the solution is cooled to 0° C. and allowed to crystallize for 1 day. White crystals are obtained as a product weighing 1.15 g. The product is a homogeneous exo epimer as shown by gas chromatography. Melting point: 62°–64° C.

$R_f$=0.47 (On DC Fertigplatten KIESELGEL thin layer of height 10 cm. developed in a saturated bath with ethyl acetate. The velocity of the solvent front is 0.7 cm./min. Developer: phosphoro-molybdenic acid.)

The mother liquor is evaporated and thus 1.95 g. of further product is obtained. According to gas chromatography the product consists of a 1:1 mixture of exo and endo epimers.

EXAMPLE 6

(−)-2,3,3aβ,6aβ-Tetrahydro-2-hexadecyloxy-5α-hydroxy-4β-(3β-hydroxy-oct-1-trans-enyl)-cyclopentano[b]furan To 2.7 g. (10 mmoles) of (−)-2,3,3aβ,6aβ-Tetrahydro-2,5α-dihydroxy-4β-(3β-hydroxy-oct-1-trans-enyl)-cyclopentano[b]furan in a 100 ml. flask, equipped with a stirrer, 5.4 ml. of dimethylsulfoxide distilled off from sodium hydride, 48 ml. of anhydrous benzene, 12.1 g. (50 mmoles) of cetyl alcohol and 0.005 ml. (0.05 mmoles) of conc. hydrochloric acid are added. The reaction is completed within ten minutes. The endo and exo epimers do not separate by chromatography. 1 ml. of 1 M sodium hydrogen carbonate solution and 225 ml. of water are added to the mixture in order to stop the reaction and remove the dimethylsulfoxide, and it is washed with 3×225 ml. of ethyl acetate. The ethyl acetate is dried and evaporated. The residue is subjected to chromatography on a 270 g. silicagel column and as eluting agent an 1:1 mixture of benzene and ethyl acetate is used. Yield: 4.55 g. (92%). $R_f$=0.63 (In the system described in Example 5).

EXAMPLE 7

(−)-2,3,3aβ,6aβ-Tetrahydro-2-exo-butoxy-5α-hydroxy-4β-(3α-hydroxy-oct-1-trans-enyl)-cyclopentano[b]furan To a 100 ml. flask equipped with a stirrer 5.06 g. (10 mmoles) of (−)-2,3,3aβ,6aβ-tetrahydro-2-exo-butoxy-5α-(p-phenylbenzoyloxy)-4β-(3α-hydroxy-oct-1-trans-enyl)-cyclopentano[b]furan are introduced. 32 ml. of anhydrous methanol and 2.1 g. (15 mmoles) of calcinated potassium carbonate are added. The temperature is kept under vigorous stirring at 40° C. The reaction is followed by thin layer chromatography. The protecting group will be split off completely within 2 to 3 hours. The reaction mixture will be cooled to 0° C. and the precipitated p-phenyl benzoic acid methyl ester is filtered off. The filtrate is evaporated in vacuo and the residue is subjected to chromatography with ethyl acetate on a silicagel column consisting of 50 g. of silicagel. Yield: 3.10 g. (95%). $R_f$ value: 0.34 (In a system described in Example 5).

EXAMPLE 8

According to Example 5, 6 and 7, 1 mmole of the corresponding starting materials is reacted with the corresponding alcohols under the described reaction circumstances and the following compounds are obtained:

(a) (−)-2,3,3aβ,6aβ-Tetrahydro-2-exo- and -endo-ethoxy-5α-hydroxy-4β-(3α- and 3β-hydroxy-oct-1-trans-enyl)-cyclopentano[b]furan, (b) (−)-2,3,3aβ,6aβ-Tetrahydro-2-exo- and -endo-isopropyloxy-5α-hydroxy-4β-(3α- and 3β-hydroxy-oct-1-trans-enyl)-cyclopentano[b]furan, (c) (−)-2,3,3aβ,6aβ-Tetrahydro-2-exo- and -endo-butoxy-5α-hydroxy-4β-(3α- and 3β-hydroxy-oct-1-trans-enyl)-cyclopentano[b]furan, (d) (−)-2,3,3aβ,6aβ-Tetrahydro-2-exo- and -endo-isobutoxy-5α-hydroxy-4β-(3α- and 3β-hydroxy-oct-1-trans-enyl)-cyclopentano[b]furan, (e) (−)-2,3,3aβ,6aβ-Tetrahydro-2-exo- and endo-terc-butoxy-5α-hydroxy-4β-(3α- and 3β-hydroxy-oct-1-trans-enyl)-cyclopentano[b]furan, (f) (−)-2,3,3aβ,6aβ-Tetrahydro-2-exo- and endo-pentyloxy-5α-hydroxy-4β-(3α- and 3β-hydroxy-oct-1-trans-enyl)-cyclopentano[b]furan, (g) (−)-2,3,3aβ,6aβ-Tetrahydro-2-exo- and -endo-hexadecyloxy-5α-hydroxy-4β-(3α- and 3β-hydroxy-oct-1-trans-enyl)-cyclopentano[b]furan.

$R_f$ values of the prepared compounds are summarized in the table below according to the above symbols. $R_f$ values of endo and exo epimers are identical. Thin layer chromatography is carried out as described in Example 5.

| Compounds | R_f values α-allyl-hydroxy | β-allyl-hydroxy |
| --- | --- | --- |
| a | 0.27 | 0.35 |
| b | 0.31 | 0.40 |
| c | 0.34 | 0.45 |
| d | 0.36 | 0.45 |
| e | 0.35 | 0.46 |
| f | 0.36 | 0.47 |
| g | 0.49 | 0.63 |

EXAMPLE 9

(−)-2,3,3aβ,6aβ-Tetrahydro-2-(2-hydroxy-ethoxy)-5α-(p-phenylbenzoyloxy)-4β-(3α-hydroxy-oct-1-trans-enyl)-cyclopentano[b]furan To a 50 ml. flask equipped with a stirrer 4.505 g. (10 mmoles) (−)-2,3,3aβ,6aβ-tetrahydro-2-hydroxy-5α-(p-phenylbenzoyloxy)-4β-(3α-hydroxy-oct-1-trans-enyl)-cyclopentano[b]furan are introduced, the starting material is dissolved in 22.5 ml. of anhydrous dimethylsulfoxide and 12.41 g. (200 mmoles) of ethylene glycol are added. The reaction is initiated by adding 0.05 ml. (0.5 mmoles) of concentrated hydrochloric acid. The conversion will be completed within 60–90 minutes. The reaction is followed by thin layer chromatography. On the chromatogram one spot is obtained, the exo and endo epimers do not separate. When the reaction is completed the reaction mixture is neutralized with 1 ml. of 1 N sodium hydrogen carbonate solution whereafter 225 ml. of water are added. The product is precipitated in the form of white needle crystals. The crystals are filtered and covered with water, dried.

Yield: 4.8 g. (97%), melting point: 113°–114° C.

Two carbonyl bands appear in the IR spectrum: at 1725 and 1700 cm$^{-1}$.

According to $C^{13}$ NMR the obtained substance is a mixture of endo and exo epimers.

$R_f$ value: 0.39 (In a system described in Example 5).

The obtained mixture of isomers is crystallized from a mixture of diisopropylether and petrolether and thus 3.4 g. of crystalline product is obtained (melting point: 119°–120° C.), which is a pure exo epimer according to $C^{13}$ NMR.

Only one carbonyl band can be found in the IR spectrum at 1700 cm$^{-1}$.

$R_f$ value: 0.39 (In a system described in Example 5).

1.4 g. of epimeric mixture is obtained by evaporation of the mother liquor in the form of an amorphous white powder.

Melting point: 80°–81° C.

EXAMPLE 10

(−)-2,3,3aβ,6aβ-Tetrahydro-2-(2,3-dihydroxy-propyloxy)-5α-(p-phenylbenzoyloxy)-4β-(3β-hydroxy-oct-1-trans-enyl)-cyclopentano[b]furan To a 50 ml. flask equipped with a stirrer 4.505 g. (10 mmoles) of (−)-2,3,3aβ,6aβ-tetrahydro-2-hydroxy-5α-(p-phenylbenzoyloxy)-4β-(3β-hydroxy-oct-1-trans-enyl)-cyclopentano[b]furan are introduced, dissolved in 22.5 ml. of anhydrous dimethylsulfoxide, 18.4 g. (200 mmoles) of glycerol and 0.05 ml. (0.5 mmole) of conc. hydrochloric acid are added. The reaction mixture is completed within 60 minutes. The reaction is followed by thin layer chromatography, and the product gives one spot as the exo and endo epimers do not separate.

The reaction is worked up by neutralizing it with 1 ml. of 1 N sodium hydrogen carbonate solution and 225 ml. of water are added. The precipitating oily product is recovered by extraction with 3×45 ml. of ether and the solvent is removed from the extract whereafter it is purified by column chromatography on a 90 g. silicagel column and as eluting agent ethyl acetate is used. Yield of the oily product: 4.9 g. (93%). The product is homogeneous on thin layer. $R_f$=0.13 (according to the method described in Example 5).

4.9 g. of oil are dissolved in the mixture of 30 ml. of diisopropylether and 15 ml. of ethyl acetate whereafter 30 ml. of petrolether are added to the solution and the exo epimer is crystallized. After cooling for three days the precipitated crystals are filtered, covered with cold diisopropylether and dried.

2.6 g. of crystalline product is obtained, which proved to be pure exo epimer.

Melting point: 92°–94° C.

2.2 g. of oily epimer mixture is obtained by evaporation of the mother liquor.

EXAMPLE 11

Different secondary and tertiary alcohols are connected with the corresponding starting materials according to Examples 9 and 10 and the following compounds are obtained:

(a) (−)-2,3,3aβ,6aβ-Tetrahydro-2-(2-hydroxy-ethoxy)-5α-(p-phenylbenzoyloxy)-4β-(3β-hydroxy-oct-1-trans-enyl)-cyclopentano[b]furan, (b) (−)-2,3,3aβ,6aβ-Tetrahydro-2-(3-hydroxy-propyloxy)-5α-(p-phenylbenzoyloxy)-4β-(3α- and 3β-hydroxy-oct-1-trans-enyl)-cyclopentano[b]furan, (c) (−)-2,3,3aβ,6aβ-Tetrahydro-2-(4-hydroxy-butyloxy)-5α-(p-phenylbenzoyloxy)-4β-(3α- and 3β-hydroxy-oct-1-trans-enyl)-cyclopentano[b]furan (d) (−)-2,3,3aβ,6aβ-Tetrahydro-2-(6-hydroxy-hexyloxy)-5α-(p-phenylbenzoyloxy)-4β-(3α- and 3β-hydroxy-oct-1-trans-enyl)-cyclopentano[b]furan, (e) (−)-2,3,3aβ,6aβ-Tetrahydro-2-(2,3-dihydroxy-propyloxy)-5α-(p-phenylbenzoyloxy)-4β-(3α-hydroxy-oct-1-trans-enyl)-cyclopentano[b]furan.

1 mmole of the starting materials is used in the reactions. $R_f$ values of the prepared compounds (thin layer chromatography is carried out according Example 5) are summarized in the table below.

| Compounds | R_f values α-allyl-hydroxy | β-allyl-hydroxy |
| --- | --- | --- |
| a | — | 0.29 |
| b | 0.41 | 0.32 |
| c | 0.42 | 0.34 |
| d | 0.46 | 0.39 |
| e | 0.19 | — |

EXAMPLE 12

(−)-2,3,3aβ,6aβ-Tetrahydro-2-exo- and endo-(2-acetoxyethoxy)-5α-(p-phenylbenzoyloxy)-4β-(3α-acetoxy-oct-1-trans-enyl)-cyclopentano[b]furan To a 100 ml. flask equipped with a stirrer, feed cone and a thermometer 2.47 g. (5 mmoles) of a crude product (a mixture of endo-exo isomers) according to Example 9 are introduced, whereafter 25 ml. of anhydrous benzene and 5.05 g. (50 mmoles) of triethyl amino are added.

To the solution 1.6 g. (20 mmoles) of acetyl chloride are dropped at room temperature under vigorous stirring. The reaction is followed by thin layer chromatography. The exo-endo epimers of the acyl product appear in two well separable spots.

When the acetylation is completed (about one hour) 50 ml. of benzene are added to the reaction mixture and it is washed with 3×25 ml. of water. The organic layer is dried, evaporated and purified by chromatography (column containing 250 g. of silicagel, eluant: a 4:1 mixture of benzene and ethyl acetate).

The solvent is removed from the fractions containing exo- and endo-epimers separately.

Yield of the exo epimer: 1.85 g. (64%).

$R_f$ value: 0.54 (Polygram ® Sil. G/UV$_{254}$ thin layer plate developing system: a 4:1 mixture of benzene and ethyl acetate).

Yield of endo epimer: 0.80 g. (27.5%).

$R_f$ value: 0.44 (in the system mentioned above).

EXAMPLE 13

(−)-2,3,3aβ,6aβ-Tetrahydro-2-exo-(2-hydroxy-ethoxy)-5α-hydroxy-4β-(3β-hydroxy-oct-1-trans-enyl)-cyclopentano[b]furan To a 50 ml. flask equipped with a stirrer and a thermometer 2.47 g. (5 mmoles) of (−)-2,3,3aβ,6aβ-tetrahydro-2-exo-(2-hydroxy-ethoxy)-5α-(p-phenyl-benzoyloxy)-4β-(3β-hydroxy-oct-1-trans-enyl)-cyclopentano[b]furan and 1.05 g. (7.5 mmoles) of calcinated potassium carbonate and 16 ml. of anhydrous methylalcohol are added.

The temperature of the reaction mixture is kept under vigorous stirring at 40° C. The reaction is followed by thin layer chromatography. The deacylation is completed within 2 hours. The reaction mixture is first cooled to 0° C., whereafter the solid parts are removed by filtration. The solvent is removed from the filtrate and the residue is purified by chromatography (column containing 15 g. of silicagel, eluent: ethyl acetate than a 2:1 mixture of ethyl acetate and acetone).

Yield: 1.4 g. (89%).

$R_f$: 0.40 (On 10 cm. high DC-Fertigplatten KIESELGEL thin layer plate in a saturated bath, developed in a 2:1 mixture of ethyl acetate and acetone. Velocity of the solvent front: 0.7 cm/min, developer: phosphoro molybdinic acid).

The product is recrystallized from ethyl acetate and petrolether and a white crystalline product is obtained.

Melting point: 63°–65° C.

EXAMPLE 14

According to Examples 7, 12 and 13 the following compounds are prepared by removing the acyl protecting groups of 5—5 mmoles of the corresponding starting materials;

(a) (−)-2,3,3aβ,6aβ-Tetrahydro-2-exo- and -endo-(2-hydroxyethoxy)-5α-hydroxy-4β-(3α- or 3β-hydroxy-oct-1-trans-enyl)-cyclopentano[b]furan;

(b) (−)-2,3,3aβ,6aβ-Tetrahydro-2-exo- and -endo-(3-hydroxypropyloxy)-5α-hydroxy-4α-(3β-hydroxy-oct-1-trans-enyl)-cyclopentano[b]furan;

(c) (−)-2,3,3aβ,6aβ-Tetrahydro-2-exo- and -endo-(4-hydroxybutoxy)-5α-hydroxy-4β-(3β-hydroxy-oct-1-trans-enyl)-cyclopentano[b]furan;

(d) (−)-2,3,3aβ,6aβ-Tetrahydro-2-exo- and -endo-(6-hydroxyhexyloxy)-5α-hydroxy-4β-(3β-hydroxy-oct-1-trans-enyl)-cyclopentano[b]furan;

(e) (−)-2,3,3aβ,6aβ-Tetrahydro-2-exo- and -endo-(2,3-dihydroxypropyloxy)-5α-hydroxy-4β-(3β-hydroxy-oct-1-trans-enyl)-cyclopentano[b]furan.

$R_f$-values are summarized in the following table. $R_f$ of the exo and endo epimers are identical. Thin layer chromatography is carried out as described in Example 13.

| Compounds | $R_f$-values α-allyl-hydroxy | β-allyl-hydroxy |
|---|---|---|
| a | 0.37 | 0.40 |
| b | — | 0.41 |
| c | — | 0.44 |
| d | — | 0.50 |
| e | — | 0.28 |

EXAMPLE 15

(−)-2,3,3aη,6aβ-Tetrahydro-2-methylthio-5α-(p-phenylbenzoyloxy)-4β-(3β-hydroxy-oct-1-trans-enyl)-cyclopentano[b]furan To a 50 ml. flask equipped with a stirrer and a thermometer 4.505 g. (10 mmoles) of (−)-2,3,3aβ,6aβ-tetrahydro-2-hydroxy-5α-(p-phenylbenzoyloxy)-4β-(3β-hydroxy-oct-1-trans-enyl)-cyclopentano[b]furan are introduced, dissolved in 9 ml. of dimethylformamide and the obtained solution is cooled to −10° to −15° C. 9.6 g. (200 mmoles) of methyl mercaptane are added and the reaction is initiated with 1 mmole of borotrifluoride etherate. The conversion takes place within a few hours. Two side products also appear in a relatively large quantity (5%) in the thin layer chromatography except the two product spots (exo and endo epimers).

The excess methyl mercaptane is distilled off from the reaction mixture at 20°–30° C. To the residue 5 ml. of 1 M sodium hydrogen carbonate solution and 45 ml. of water are added whereafter the product is obtained by extraction with 3×45 ml. of ether. The solvent is removed from the extract and the residue is subjected to column chromatography on 450 g. silicagel column, as eluting agent a 4:1 mixture of benzene and ethyl acetate is employed.

The solvent is removed separately from the fractions containing endo and exo epimers.

Yield of the exo epimer: 2.40 g. (50%). The product is a thick oil, $R_f$=0.53 (in the system described in Example 1).

The oil is crystallized from a system of diisopropylether and petrolether and thus white crystals are obtained. Melting point: 72°–73° C.

Yield of the obtained endo epimer: 1.60 g. (33%), $R_f$=0.35 (in a system described in Example 1).

EXAMPLE 16

(−)-2,3,3aβ,6aβ-Tetrahydro-2-exo and endo-butylthio-5α-(p-phenylbenzoyloxy)-4β-(3β-hydroxy-oct-1-trans-enyl)-cyclopentano[b]furan and
(−)-2,3,3aβ,6aβ-tetrahydro-2-exo- and -endo-phenylthio-5α-(p-phenylbenzoyloxy)-4β-(3β-hydroxy-oct-1-trans-enyl)-cyclopentano[b]furan The tital compounds are prepared by connecting the suitable mercaptanes according to Example 15.

$R_f$-values are summarized in the table below:

| Compounds | R_f values exo epimer | endo epimer |
|---|---|---|
| butylthio derivative | 0.61 | 0.44 |
| phenylthio derivative | 0.60 | 0.45 |

EXAMPLE 17

(−)-2,3,3aβ,6aβ-Tetrahydro-2-exo-butylthio-5α-hydroxy-4β-(3β-hydroxy-oct-1-trans-enyl)-cyclopentano[b]furan 2.61 g. (5 mmoles) of (−)-2,3,3aβ,6aβ-tetrahydro-2-exo-butylthio-5α-(p-phenylbenzoyloxy)-4β-(3β-hydroxy-oct-1-trans-enyl)-cyclopentano[b]furan are used as starting material and according to Example 7 the title compound is obtained. The chromatography is carried out with a 1:1 mixture of benzene and ethyl acetate as eluent.

Yield of the title compound: 1.55 g. (91%). The oil crystallizes on cooling. Melting point: 55°–57° C. R_f values measured according to Example 5: 0.49.

EXAMPLE 18

The following compounds are obtained according to the method described in Example 1. As a reactant the corresponding alcohol is employed.

(a) (−)-2,3,3aβ,6aβ-Tetrahydro-2-exo- and -endo-benzyloxy-5α-(p-phenylbenzoyloxy)-4β-(3β-hydroxy-oct-1-trans-enyl)-cyclopentano[b]furan;

(b) (−)-2,3,3aβ,6aβ-Tetrahydro-2-exo and -endo-(2-chloroethoxy)-5α-(p-phenylbenzoyloxy)-4β-(3β-hydroxy-oct-1-trans-enyl)-cyclopentano[b]furan;

(c) (−)-2,3,3aβ,6aβ-Tetrahydro-2-exo- and -endo-allyloxy-5α-(p-phenylbenzoyloxy)-4β-(3β-hydroxy-oct-1-trans-enyl)-cyclopentano[b]furan.

R_f values are given in the following table (thin layer chromatography according to Example 1).

| Compounds | R_f values exo epimer | endo epimer |
|---|---|---|
| a | 0.61 | 0.45 |
| b | 0.55 | 0.375 |
| c | 0.55 | 0.42 |

EXAMPLE 19

(−)-2,3,3aβ,6aβ-Tetrahydro-2-(p-phenylbenzoyloxy)-5α-hydroxy-4β-(3α- and 3β-hydroxy-oct-1-trans-enyl)-cyclopentano[b]furan To a 50 ml. flask equipped with a stirrer 2.7 g. (10 mmoles) of (−)-2,3,3aβ,6aβ-tetrahydro-2,5α-dihydroxy-4β-(3α-hydroxy-oct-1-trans-enyl)-cyclopentano[b]furan, 2.75 g. (15 mmoles) of p-phenylbenzyl alcohol and 14 ml. of anhydrous dimethylsulfoxide are added. The reaction is started by adding 0.1 ml. (1 mmole) of concentrated hydrochloric acid. The conversion is completed within 60–90 minutes. 2 ml. of 1 M sodium hydrogen carbonate solution and 140 ml. of water are added to the reaction mixture whereafter it is extracted with 3×28 ml. of ethyl acetate. The organic layer is dried and the solvent is removed by evaporation in vacuo. The residue is subjected to chromatography on a silicagel column weighing 270 g. and as eluent ethyl acetate is used.

Yield of the 3α title product: 3.8 g. (87%).

R_f value: 0.35 (POLYGRAM ® Sil. G/UF_254 thin layer plate, developed with ethyl acetate).

p-Phenylbenzyl alcohol gives R_f=0.82 in the same system.

When using the corresponding 3β-compound as starting material, the 3β-epimer of the title compound is obtained according to the process described above.

Yield: 3.9 (89%). R_f value=0.56 (in the above system).

EXAMPLE 20

(−)-2,3,3aβ6aβ-Tetrahydro-2-acetoxy-5α-acetoxy-4β-(3β-acetoxy-oct-1-trans-enyl)-cyclopentano[b]furan To a 100 ml. flask equipped with a stirrer and a dropping funnel 2.7 g. (10 mmoles) of (−)-2,3,3aβ,6aβ-tetrahydro-2,5α-dihydroxy-4β-(3β-hydroxy-oct-1-trans-enyl)cyclopentano[b]furan, 50 ml. of ethyl acetate and 8 ml. (100 mmoles) of anhydrous pyridine are added. 5.3 ml. of (75 mmoles) of freshly distilled acetyl chloride are dropped from the dropping funnel within about half an hour. The reaction is followed by thin layer chromatography with a 2:1 mixture of benzene and ethyl acetate.

The reaction is completed in an hour. Substantially no side-product is formed. The reaction mixture is stirred with 100 ml. of water and shaken out with 3×50 ml. of ethyl acetate. The ethyl acetate layer is dried and evaporated. The residue is subjected to chromatography on a silicagel column weighing 150 g. and eluted with a 3:1 mixture of benzene and ethyl acetate. The obtained product is a thick colorless oil which does not crystallise.

Yield: 3.4 g. (87%).

R_f value: 0.74 (in a system described in Example 1).

EXAMPLE 21

(−)-2,3,3aβ,6aβ-Tetrahydro-2-(2-hydroxy-3-chloropropyloxy)-5α-acetoxy-4β-(3β-acetoxy-oct-1-trans-enyl)-cyclopentano[b]-furan To a 50 ml. flask equipped with a stirrer 3.9 g. (10 mmoles) of (−)-2,3,3aβ,6aβ-tetrahydro-2-acetoxy-5α-acetoxy-4β-(3β-acetoxy-oct-1-trans-enyl)-cyclopentano[b]furan are introduced, and dissolved in 15 ml. dimethylsulfoxide obtained by distillation of sodium hydride.

2.5 ml. (30 mmoles) of 3-chloro-1,2-propane-diol are added and 0.05 ml. (0.5 mmoles) of concentrated hydrochloric acid is used to start the reaction. The reaction is followed by thin layer chromatography with a 4:1 mixture of isopropylether and ethyl acetate. The exo- and endoepimers are separated by chromatography. The conversion is completed within 10 minutes.

In order to stop the reaction and to remove dimethylsulphoxide 1 ml. 1 M sodium hydrogen carbonate solution and 100 ml. of water are added to the mixture whereafter the mixture is extracted with 3×30 ml. of ethyl acetate. The ethyl acetate layer is extracted with 3×30 ml. of ethyl acetate. The ethyl acetate layer is dried and evaporated. The residue is subjected to chromatography on silicagel column weighing 300 g. and eluted with a 5:1 mixture of diisopropylether and ethyl acetate.

The obtained ex-epimer is a thick oil, which does not crystallize.

Yield: 1.9 g. (42.5%).

$R_f$ value: 0.35 (On a DC-Fertigplatten KIESELGEL thin layer plate, in a saturated bath, developed by a 4:1 mixture of isopropylether and ethyl acetate. Developer: phosphoro molybdenic acid.)

The obtained endo epimer is a thick, colorless oil, which does not crystallize.

Yield: 1.7 g. (38%).

$R_f$ value: 0.28 (In a system described at the exo epimer).

EXAMPLE 22

(−)-2,3,3aβ,6aβ-Tetrahydro-2-(2-hydroxy-3-chloro-propyloxy)-5α-(p-phenylbenzoyloxy)-4β-(3β-hydroxy-oct-1-trans-enyl)cyclopentano[b]furan 10 mmoles of (−)-2,3,3aβ,6aβ-tetrahydro-2-hydroxy-5α-(p-phenylbenzoyloxy)-4β-(3β-hydroxy-oct-1-trans-enyl)-cyclopentano[b]furan are reacted with 3-chloro-1,2-propanediol as described in Example 21 and the exo and endo epimers of the title compound are prepared.

The obtained exo epimer is a thick and colourless oil which does not crystallise.

Yield: 2.5 g. (45%).

$R_f$ value: 0.48. (On a DC-Fertigplatten KIESELGEL thin layer plate of height 10 cm. in a saturated bath, developed with a 1:2 mixture of benzene and ethyl acetate. Developer: phosphoro molybdenic acid).

The obtained endo epimer is a thick and colorless oil, which does not crystallize.

Yield: 2.2 g. (40%).

$R_f$ value: 0.38 (in the system described at the exo epimer).

EXAMPLE 23

(−)-2,3,3a≠,6aβ-Tetrahydro-2-exo-(2,3-epoxy-propyloxy)-5α-hydroxy-4β-(3β-hydroxy-oct-1-trans-enyl)-cyclopentano[b]furan To a 100 ml. flask equipped with a stirrer 2.23 g. (5 mmoles) of (−)-2,3,3aβ,6aβ-tetrahydro-2-exo-(2-hydroxy-3-chloro-propyloxy)-5α-acetoxy-4β-(3β-acetoxy-oct-1-trans-enyl)-cyclopentano[b]furan are added. 30 ml. of acetone and 30 ml. of 2 N potassium hydroxide solution are further added. The reaction mixture is stirred at room temperature and the reaction is followed by thin layer chromatography. The reaction is completed within 1.5–2 hours. The reaction mixture is then stirred with 250 ml. of water and extracted with 2×100 ml. of ethyl acetate. The ethyl acetate layer is dried and evaporated. The residue is chromatographed with ethyl acetate as eluent on a silicagel column weighing 250 g.

Yield of the obtained exo epimer: 1.4 g. (86%).

$R_f$ value: 0.42. (in a system as described in Example 5).

EXAMPLE 24

(−)-2,3,3aβ,6aβ-Tetrahydro-2-(4-ethoxycarbonyl-butyloxy)-5α-hydroxy-4β-(3β-hydroxy-oct-1-trans-enyl)-cyclopentano[b]furan To a 25 ml. flask equipped with a stirrer 2.7 g. (10 mmoles) of (−)-2,3,3aβ,6aβ-tetrahydro-2,5α-dihydroxy-4β-(3β-hydroxy-oct-1-trans-enyl)-cyclopentano[b]furan, 2.7 ml. of anhydrous dimethylsulphoxide and 1.61 g. (11 mmoles) of 4-ethoxycarbonyl-butylalcohol are added and 0.05 ml. (0.5 mmole) concentrated hydrochloric acid is given to initiate the reaction. The conversion is completed within 15 minutes. 1 ml. of 1 M sodium hydrogen carbonate solution and 27 ml. of water are then added to the reaction mixture and it is extracted with 3×27 ml. of ethyl acetate. When the ethyl acetate is removed by evaporation the residue is chromatographed on a silicagel column weighing 270 g. and as an eluent ethyl acetate is used.

Yield of the exo epimer: 2.20 g. (55%). $R_f$ value: 0.57 (in a system as described in Example 19).

Yield of the endo epimer: 1.35 g. (34%). $R_f$ value: 0.50 (in a system as described in Example 19).

EXAMPLE 25

(−)-2,3,3aβ,6aβ-Tetrahydro-2-(2-diisopropylamino-ethyloxy)-5α-(p-phenylbenzoyloxy)-4β-(3β-hydroxy-oct-1-trans-enyl)-cyclopentano[b]furan To a 25 ml. flask equipped with a stirrer 2.25 g. (5 mmoles) of (−)-2,3,3aβ,6aβ-tetrahydro-2-hydroxy-5α-(p-phenylbenzoyloxy)-4β-(3β-hydroxy-oct-1-trans-enyl)-cyclopentano[b]furan, 2.25 ml. of anhydrous dimethylsulfoxide, 7.25 g. (50 mmoles) of 2-diisopropyla-mine-ethyl alcohol are added and 0.05 ml. (0.5 mmoles) concentrated hydrochloric acid is also added to start the reaction. The acetal formation is completed within 60 minutes. The exo and endo epimers of the product appear separately on the thin layer chromatogram. When the reaction is completed the reaction mixture is neutralized with 1 ml. of 1 M sodium hydrogen carbonate solution and 72 ml. of water are added and the product is extracted with 3×36 ml. of ethyl acetate. The ethyl acetate is evaporated on a silicagel column weighing 225 g. and as eluting agent a 2:1 mixture of benzene and ethyl acetate is used.

Yield of the exo epimer: 1.6 g. (56%).

$R_f$ value=0.43 (in a system described in Example 1).

Yield of the endo epimer: 1.1 g. (38%).

$R_f$ value=0.32 (in a system described in Example 1).

What we claim is:

1. A racemic or optically active compound of the formula:

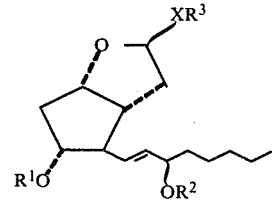

wherein
 X is oxygen or sulfur;
 $R^1$ is hydrogen, $C_1$ to $C_4$ alkanoyl, benzoyl or phenyl-substituted benzoyl;
 $R^2$ is hydrogen or $C_1$ to $C_4$ alkanoyl; and where X is oxygen,
 $R^3$ is $C_2$ to $C_{40}$ straight or branched chain alkyl substituted by hydroxy, epoxy, amino, $C_1$ to $C_6$ alkylamino, $C_1$ to $C_6$ dialkylamino, $C_1$ to $C_6$ alkanoyloxy or $C_1$ to $C_4$ alkoxycarbonyl; cyclohexyl, phenyl unsubstituted or substituted by halogen, amino, $C_1$ to $C_4$ alkyl-substituted amino, $C_1$ to $C_4$ alkoxy, nitro, or hydroxy; $C_1$ to $C_6$ alkanoyl; allyl; or phenyl-$C_1$ to $C_4$ alkyl unsubstituted or substituted by a $C_2$ to $C_6$ alkene group; or where X is sulfur $R^3$ is as defined above or is $C_1$ to $C_{40}$ straight or branched chain alkyl; and ~ represents the exo- or endo-steric position in the ring and indicates an α- or β-steric position in the side chain.

2. The compound selected from the group consisting of:
(1) (−)-2,3,3-a,β-6a,β-tetrahydro-2-(2-hydroxyethoxy) or cyclohexyloxy-5α-(p-phenylbenzoyloxy)-4β-(3α-hydroxy-oct-1-trans-enyl)-cyclopentano(b)furan;
(2) (−)-2,3,3-a,β-6a,β-tetrahydro-2-(2,3-dihydroxypropoxy)-5α-(p-phenylbenzoyloxy)-4β-(3β-hydroxy-oct-1-trans-enyl)-cyclopentano(b)furan;
(3) (−)-2,3,3-a,β-6a,β-tetrahydro-2-(2-hydroxyethoxy)-5α-(p-phenylbenzoyloxy)-4β-(3β-hydroxy-oct-1-trans-enyl)-cyclopentano(b)furan;
(4) (−)-2,3,3-a,β-6a,β-tetrahydro-2-(3-hydroxypropyloxy)-5α-(p-phenylbenzoyloxy)-4β-(3α- or -β-hydroxy-oct-1-trans-enyl)-cyclopentano(b)furan;
(5) (−)-2,3,3-a,β-6a,β-tetrahydro-2-(4-hydroxybutyloxy)-5α-(p-phenylbenzoyloxy)-4β-(3α- or -β-hydroxy-oct-1-trans-enyl)-cyclopentano(b)furan;
(6) (−)-2,3,3-a,β-6a,β-tetrahydro-2-(6-hydroxy-hexyloxy)-5α-(p-phenylbenzyloxy)-4β-(3α- or β-hydroxy-oct-1-trans-enyl)-cyclopentano(b)furan;
(7) (−)-2,3,3-a,β-6a,β-tetrahydro-2-(2,3-dihydroxypropyloxy)-5α-(p-phenylbenzoyloxy)-4β-(3α-hydroxy-oct-1-trans-enyl)-cyclopentano(b)furan;
(8) (−)-2,3,3-a,β-6a,β-tetrahydro-2-exo- or -endo-(2-acetoxy)-5α-(p-phenylbenzoyloxy)-4β-(3α-acetoxy-oct-1-trans-enyl)-cyclopentano(b)furan;
(9) (−)-2,3,3-a,β-6a,β-tetrahydro-2-exo-(2-hydroxyethoxy)-5α-hydroxy-4β-(3β-hydroxy-oct-1-trans-enyl)-cyclopentano(b)furan;
(10) (−)-2,3,3-a,β-6a,β-tetrahydro-2-exo- or -endo-(2-hydroxy-ethoxy)-5α-hydroxy-4β-(3α- or -β-hydroxy-oct-1-trans-enyl)-cyclopentano(b)furan;
(11) (−)-2,3,3-a,β-6a,β-tetrahydro-2-exo- or -endo-(3-hydroxy-propyloxy)-5α-hydroxy-4β-(3β-hydroxy-oct-1-trans-enyl)-cyclopentano(b)furan;
(12) (−)-2,3,3-a,β-6a,β-tetrahydro-2-exo- or -endo-(4-hydroxy-butyloxy)-5α-hydroxy-4β-(3β-hydroxy-oct-1-trans-enyl)-cyclopentano(b)furan;
(13) (−)-2,3,3-a,β-6a,β-tetrahydro-2-exo- or -endo-(6-hydroxy-hexyloxy)-5α-hydroxy-4β-(3β-hydroxy-oct-1-trans-enyl)-cyclopentano(b)furan;
(14) (−)-2,3,3-a,β-6a,β-tetrahydro-2-exo- or -endo-(2,3-dihydroxypropyloxy)-5α-hydroxy-4β-(3β-hydroxy-oct-1-trans-enyl)-cyclopentano(b)furan;
(15) (−)-2,3,3-a,β-6a,β-tetrahydro-2-methylthio-5α-(p-phenylbenzoyloxy)-4β-(3β-hydroxy-oct-1-trans-enyl)-cyclopentano(b)furan;
(16) (−)-2,3,3-a,β-6a,β-tetrahydro-2-exo- or -endo-butylthio-5α-(p-phenylbenzoyloxy)-4β-(3β-hydroxy-oct-1-trans-enyl)-cyclopentano(b)furan;
(17) (−)-2,3,3-a,β-6a,β-tetrahydro-2-exo- or -endo-phenylthio-5α-(p-phenylbenzoyloxy)-4β-(3β-hydroxy-oct-1-trans-enyl)-cyclopentano(b)furan;
(18) (−)-2,3,3-a,β-6a,β-tetrahydro-2-exo-butylthio-5α-hydroxy-4β-(3β-hydroxy-oct-1-trans-enyl)-cyclopentano(b)furan;
(19) (−)-2,3,3-a,β-6a,β-tetrahydro-2-exo- or -endo-benzoyloxy-5α-(p-phenylbenzoyloxy)-4β-(3β-hydroxy-oct-1-trans-enyl)-cyclopentano(b)furan;
(20) (−)-2,3,3-a,β-6a,β-tetrahydro-2-exo- or -endo-(2-chloroethoxy)-5α-(p-phenylbenzoyloxy)-4β-(3β-hydroxy-oct-1-trans-enyl)-cyclopentano(b)furan;
(21) (−)-2,3,3-a,β-6a,β-tetrahydro-2-exo- or -endo-allyloxy-5α-(p-phenylbenzoyloxy)-4β-(3β-hydroxy-oct-1-trans-enyl)-cyclopentano(b)furan;
(22) (−)-2,3,3-a,β-6a,β-tetrahydro-2-(p-phenylbenzoyloxy)-5α-hydroxy-4β-(3α- or -β-hydroxy-oct-1-trans-enyl)-cyclopentano(b)furan;
(23) (−)-2,3,3-a,β-6a,β-tetrahydro-2-acetoxy-5α-acetoxy-4β-(3β-acetoxy-oct-1-trans-enyl)-cyclopentano(b)furan;
(24) (−)-2,3,3-a,β-6a,β-tetrahydro-2-(2-hydroxy-3-chloro-propyloxy)-5α-acetoxy-4β-(3β-acetoxy-oct-1-trans-enyl)-cyclopentano(b)furan;
(25) (−)-2,3,3-a,β-6a,β-tetrahydro-2-(2-hydroxy-3-chloro-propyloxy)-5α-(p-phenylbenzoyloxy)-4β-(3β-hydroxy-oct-1-trans-enyl)-cyclopentano(b)furan;
(26) (−)-2,3,3-a,β-6a,β-tetrahydro-2-exo-(2,3-epoxy-propyloxy)-5α-hydroxy-4β-(3β-hydroxy-oct-1-trans-enyl)-cyclopentano(b)furan;
(27) (−)-2,3,3-a,β-6a,β-tetrahydro-2-(4-ethoxycarbonyl-butyloxy)-5α-hydroxy-4β-(3β-hydroxy-oct-1-trans-enyl)-cyclopentano(b)furan; and
(28) (−)-2,3,3-a,β-6a,β-tetrahydro-2-(2-diisopropylamino-ethyloxy)-5α-(p-phenylbenzoyloxy)-4β-(3β-hydroxy-oct-1-trans-enyl)-cyclopentano(b)furan.

3. A racemic or optically active compound of the formula:

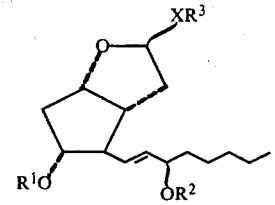

wherein
X is oxygen or sulfur;
$R^1$ is hydrogen, $C_1$ to $C_4$ alkanoyl, benzoyl or phenyl-substituted benzoyl;
$R^2$ is hydrogen or $C_1$ to $C_4$ alkanoyl;
$R^3$ is $C_2$ to $C_{20}$ straight or branched chain alkyl substituted by hydroxy, epoxy, amino, $C_1$ to $C_6$ alkylamino, $C_1$ to $C_6$ dialkylamino, $C_1$ to $C_6$ alkanoyloxy or $C_1$ to $C_4$ alkoxycarbonyl; phenyl unsubstituted or substituted by halogen, amino, $C_1$ to $C_4$ alkyl-substituted amino, $C_1$ to $C_4$ alkoxy, nitro, or hydroxy; $C_1$ to $C_6$ alkanoyl, allyl or phenyl-$C_1$ to $C_4$ alkyl unsubstituted or substituted by a $C_2$ to $C_6$ alkene group; and
~ represents the exo- or endo-steric position in the ring and indicates an α- or β-steric position in the side chain.

4. The compound selected from the group consisting of:
(1) (−)-2,3,3-a,β-6a,β-tetrahydro-2-(2-hydroxyethoxy)-5α-(p-phenylbenzoyloxy)-4β-(3β-hydroxy-oct-1-trans-enyl)-cyclopentano(b)furan;
(2) (−)-2,3,3-a,β-6a,β-tetrahydro-2-(2,3-dihydroxypropoxy)-5α-(p-phenylbenzoyloxy)-4β-(3β-hydroxy-oct-1-trans-enyl)-cyclopentano(b)furan;

(3) (−)-2,3,3-a,β-6a,β-tetrahydro-2-(2-hydroxy-ethoxy)-5α-(p-phenylbenzoyloxy)-4β-(3β-hydroxy-oct-1-trans-enyl)-cyclopentano(b)furan;

(4) (−)-2,3,3-a,β-6a,β-tetrahydro-2-(3-hydroxy-propyloxy)-5α-(p-phenylbenzoyloxy)-4β-(3α- or -β-hydroxy-oct-1-trans-enyl)-cyclopentano(b)furan;

(5) (−)-2,3,3-a,β-6a,β-tetrahydro-2-(4-hydroxy-butyloxy)-5α-(p-phenylbenzoyloxy)-4β-(3α- or -β-hydroxy-oct-1-trans-enyl)-cyclopentano(b)furan;

(6) (−)-2,3,3-a,β-6a,β-tetrahydro-2-(6-hydroxy-hexyloxy)-5α-(p-phenylbenzoyloxy)-4β-(3α- or -β-hydroxy-oct-1-trans-enyl)-cyclopentano(b)furan;

(7) (−)-2,3,3-a,β-6a,β-tetrahydro-2-(2,3-dihydroxy-propyloxy)-5α-(p-phenylbenzoyloxy)-4β-(3β-hydroxy-oct-1-trans-enyl)-cyclopentano(b)furan;

(8) (−)-2,3,3-a,β-6a,β-tetrahydro-2-exo- or -endo-(2-acetoxy)-5α-(p-phenylbenzoyloxy)-4β-(3α-acetoxy-oct-1-trans-enyl)-cyclopentano(b)furan;

(9) (−)-2,3,3-a,β-6a,β-tetrahydro-2-exo-(2-hydroxy-ethoxy)-5α-hydroxy-4β-(3β-hydroxy-oct-1-trans-enyl)-cyclopentano(b)furan;

(10) (−)-2,3,3-a,β-6a,β-tetrahydro-2-exo- or -endo-(2-hydroxy-ethoxy)-5α-hydroxy-4β-(3α- or -β-hydroxy-oct-1-trans-enyl)-cyclopentano(b)furan;

(11) (−)-2,3,3-a,β-6a,β-tetrahydro-2-exo- or -endo-(3-hydroxy-propyloxy)-5α-hydroxy-4β-(3β-hydroxy-oct-1-trans-enyl)-cyclopentano(b)furan;

(12) (−)-2,3,3-a,β-6a,β-tetrahydro-2-exo- or -endo-(4-hydroxybutyloxy)-5α-hydroxy-4β-(3β-hydroxy-oct-1-trans-enyl)-cyclopentano(b)furan;

(13) (−)-2,3,3-a,β-6a,β-tetrahydro-2-exo- or -endo-(6-hydroxy-hexyloxy)-5α-hydroxy-4β-(3β-hydroxy-oct-1-trans-enyl)-cyclopentano(b)furan;

(14) (−)-2,3,3-a,β-6a,β-tetrahydro-2-exo- or -endo-(2,3-dihydroxypropyloxy)-5α-hydroxy-4β-(3β-hydroxy-oct-1-trans-enyl)-cyclopentano(b)furan;

(15) (−)-2,3,3-a,β-6a,β-tetrahydro-2-exo- or -endo-phenylthio-5α-(p-phenylbenzoyloxy)-4β-(3β-hydroxy-oct-1-trans-enyl)-cyclopentano(b)furan;

(16) (−)-2,3,3-a,β-6a,β-tetrahydro-2-exo- or -endo-benzoyloxy-5α-(p-phenylbenzoyloxy)-4β-(3β-hydroxy-oct-1-trans-enyl)-cyclopentano(b)furan;

(17) (−)-2,3,3-a,β-6a,β-tetrahydro-2-exo- or -endo-(2-chloroethoxy)-5α-(p-phenylbenzoyloxy)-4β-(3β-hydroxy-oct-1-trans-enyl)-cyclopentano(b)furan;

(18) (−)-2,3,3-a,β-6a,β-tetrahydro-2-exo- or -endo-allyloxy-5α-(p-phenylbenzoyloxy)-4β-(3β-hydroxy-oct-1-trans-enyl)-cyclopentano(b)furan;

(19) (−)-2,3,3-a,β-6a,β-tetrahydro-2-(p-phenylbenzoyloxy)-5α-hydroxy-4β-(3α- or -β-hydroxy-oct-1-trans-enyl)-cyclopentano(b)furan;

(20) (−)-2,3,3-a,β-6a,β-tetrahydro-2-acetoxy-5α-acetoxy-4β-(3β-acetoxy-oct-1-trans-enyl)-cyclopentano(b)furan;

(21) (−)-2,3,3-a,β-6a,β-tetrahydro-2-(2-hydroxy-3-chloro-propyloxy)-5α-acetoxy-4β-(3β-acetoxy-oct-1-trans-enyl)-cyclopentano(b)furan;

(22) (−)-2,3,3-a,β-6a,β-tetrahydro-2-(2-hydroxy-3-chloro-propyloxy)-5α-(p-phenylbenzoyloxy)-4β-(3β-hydroxy-oct-1-trans-enyl)-cyclopentano(b)furan;

(23) (−)-2,3,3-a,β-6a,β-tetrahydro-2-exo-(2,3-epoxy-propyloxy)-5α-hydroxy-4β-(3β-hydroxy-oct-1-trans-enyl)-cyclopentano(b)furan;

(24) (−)-2,3,3-a,β-6a,β-tetrahydro-2-(4-ethoxycarbonyl-butyloxy)-5α-hydroxy-4β-(3β-hydroxy-oct-1-trans-enyl)-cyclopentano(b)furan; and

(25) (−)-2,3,3-a,β-6a,β-tetrahydro-2-(2-diisopropyl-amino-ethyloxy)-5α-(p-phenylbenzoyloxy)-4β-(3β-hydroxy-oct-1-trans-enyl)-cyclopentano(b)furan.

* * * * *